United States Patent
Hartwell

(10) Patent No.: US 10,383,967 B2
(45) Date of Patent: Aug. 20, 2019

(54) SUBSTANCE SENSING WITH TRACERS

(71) Applicant: INVENSENSE, INC., San Jose, CA (US)

(72) Inventor: Peter G. Hartwell, Menlo Park, CA (US)

(73) Assignee: INVENSENSE, INC., San Jose, CA (US)

( * ) Notice: Subject to any disclaimer, the term of this patent is extended or adjusted under 35 U.S.C. 154(b) by 62 days.

(21) Appl. No.: 15/365,818

(22) Filed: Nov. 30, 2016

(65) Prior Publication Data
US 2018/0147311 A1 May 31, 2018

(51) Int. Cl.
*A61L 9/015* (2006.01)
*G01N 33/00* (2006.01)

(52) U.S. Cl.
CPC .......... *A61L 9/015* (2013.01); *G01N 33/0004* (2013.01); *A61L 2209/111* (2013.01)

(58) Field of Classification Search
CPC ... A61L 9/015; A61L 2209/111; G01N 27/04; G01N 33/0073; G05D 7/0617; F24F 2003/1689; F24F 2110/00
See application file for complete search history.

(56) References Cited

U.S. PATENT DOCUMENTS

| | | | | |
|---|---|---|---|---|
| 4,229,415 A | * | 10/1980 | Bryson | A01M 13/00 239/34 |
| 5,409,839 A | * | 4/1995 | Balestrieri | D21H 21/43 436/27 |

(Continued)

FOREIGN PATENT DOCUMENTS

| CN | 102778478 A | 11/2012 |
|---|---|---|
| CN | 103332726 A | 10/2013 |

(Continued)

OTHER PUBLICATIONS

Wilson, Alphus D., and Manuela Baietto. "Applications and advances in electronic-nose technologies." Sensors 9.7 (2009): 5099-5148.*

(Continued)

*Primary Examiner* — Jonathan M Dunlap
(74) *Attorney, Agent, or Firm* — Amin, Turocy & Watson, LLP

(57) ABSTRACT

Emission of a scented substance, which is mixed with a tracer substance, is controlled based on an amount of the tracer substance sensed during the emission of the scented substance. The scented substance can be mixed with the tracer substance in a known defined ratio. When the mixture of the scented substance and tracer substance is being emitted by a device, a substance sensor component can sense the amount of the tracer substance being emitted. An emission management component can control the emission of the mixture of substances based on the amount of the tracer substance detected to facilitate controlling the amount of the scented substance being emitted. The emission management component also can control emission of the scented substance in a defined area based on the tracer substance and environmental conditions in the defined area. The tracer substance can be safe, colorless, and/or odorless with respect to people.

20 Claims, 8 Drawing Sheets

(56) References Cited

U.S. PATENT DOCUMENTS

| | | | |
|---|---|---|---|
| 5,724,256 A * | 3/1998 | Lee | A61L 9/125 422/105 |
| 5,776,425 A | 7/1998 | Wu et al. | |
| 6,111,280 A | 8/2000 | Gardner et al. | |
| 6,259,350 B1 | 7/2001 | Mueller-Fiedler et al. | |
| 6,282,458 B1 * | 8/2001 | Murayama | A61L 9/122 422/108 |
| 6,347,414 B2 * | 2/2002 | Contadini | E03D 9/002 4/222 |
| 6,553,777 B2 * | 4/2003 | Dillenback | A61L 9/02 62/171 |
| 6,628,204 B1 * | 9/2003 | Ito | G09B 9/00 340/691.2 |
| 7,610,118 B2 * | 10/2009 | Schramm | A01M 1/2033 239/69 |
| 8,392,029 B2 * | 3/2013 | Nakamoto | G01N 1/38 700/283 |
| 9,352,065 B2 * | 5/2016 | Habbel | A61L 2/00 |
| 9,377,786 B2 * | 6/2016 | Nakamoto | G05D 11/132 |
| 9,439,995 B2 * | 9/2016 | Conroy | G06Q 10/08 |
| 9,691,214 B2 * | 6/2017 | Chan | G07F 17/0014 |
| 9,827,343 B2 * | 11/2017 | Lima | A61L 9/037 |
| 9,860,690 B2 * | 1/2018 | Bak | H04W 4/04 |
| 2001/0029781 A1 | 10/2001 | Tai et al. | |
| 2002/0119093 A1 | 8/2002 | Murayama et al. | |
| 2005/0185392 A1 * | 8/2005 | Walter | A61L 9/037 362/96 |
| 2005/0199041 A1 | 9/2005 | Weber et al. | |
| 2006/0154401 A1 | 7/2006 | Gardner et al. | |
| 2006/0231882 A1 | 10/2006 | Kim et al. | |
| 2007/0258849 A1 * | 11/2007 | Kent | A61L 9/035 422/5 |
| 2009/0126460 A1 | 5/2009 | Gardner et al. | |
| 2010/0044453 A1 * | 2/2010 | Porchia | A01M 1/205 239/6 |
| 2011/0226864 A1 * | 9/2011 | Kim | A61L 9/14 239/6 |
| 2012/0046790 A1 * | 2/2012 | Anderson | A01M 1/2022 700/266 |
| 2012/0288987 A1 | 11/2012 | Radu et al. | |
| 2013/0075255 A1 | 3/2013 | Moon et al. | |
| 2014/0208828 A1 | 7/2014 | Von Waldkirch | |
| 2014/0208830 A1 | 7/2014 | Buhler et al. | |
| 2015/0056426 A1 | 2/2015 | Grouchko et al. | |
| 2016/0038908 A1 | 2/2016 | Cobianu et al. | |
| 2016/0187279 A1 | 6/2016 | Tayebi et al. | |
| 2016/0187280 A1 | 6/2016 | Potyralio et al. | |
| 2016/0370263 A1 * | 12/2016 | Duesterhoft | B64C 39/024 |
| 2017/0067841 A1 | 3/2017 | Liu et al. | |
| 2017/0168000 A1 | 6/2017 | Ichiki | |
| 2018/0028985 A1 * | 2/2018 | Ansley | A61L 9/14 |

FOREIGN PATENT DOCUMENTS

| | | |
|---|---|---|
| CN | 104316566 A | 1/2015 |
| EP | 2762864 A1 | 8/2014 |
| GB | 2464016 A | 4/2010 |
| KR | 20030087853 A | 11/2003 |
| WO | 0075649 A1 | 12/2000 |

OTHER PUBLICATIONS

Nakaizumi, Fumitaka, et al. "SpotScents: A novel method of natural scent delivery using multiple scent projectors." Virtual Reality Conference, 2006. IEEE, 2006.*

Nakamoto, T., and H. Hiramatsu. "Study of odor recorder for dynamical change of odor using QCM sensors and neural network." Sensors and Actuators B: Chemical 85.3 (2002): 263-269.*

Choi, Jongwoo, et al. "The Wireless Electronic Noses and Mobile Devices Interoperation Based on Internet of Things Technology." (2015).*

Office Action for U.S. Appl. No. 15/000,729 dated Oct. 17, 2016, 22 pages.

Partial International Search Report dated Oct. 25, 2016 for PCT Application Serial No. PCT/US2016/047359, 8 pages.

Simon, et al., "Micromachined Metal Oxide Gas Sensors: Opportunities To Improve Sensor Performance", Sensors and Actuators B: Chemical: International Journal Devoted To Research And Development Of Physical And Chemical Transducers, Elsevier BV, NL, vol. B73, No. 1, Feb. 25, 2001 (Feb. 25, 2001), pp. 1-26, XP001120244.

Bhattacharyya, "Technological Journey Towards Reliable Microheater Development for MEMS Gas Sensors: A Review," IEEE Transactions on Device and Materials Reliability, vol. 14, No. 2, Jun. 2014, 11 pages.

Frey, et al., "A Digital CMOS Architecture for a Micro-Hotplate Array," IEEE Journal of Solid-State Circuits, vol. 42, No. 2, Feb. 2007, 10 pages.

Office Action for U.S. Appl. No. 15/000,729 dated May 17, 2017, 21 pages.

Office Action for U.S. Appl. No. 14/849,551 dated May 30, 2017, 25 pages.

Office Action for U.S. Appl. No. 14/849,551 dated Jul. 27, 2017, 16 pages.

Office Action for U.S. Appl. No. 15/000,729 dated Dec. 15, 2017, 25 pages.

Office Action for U.S. Appl. No. 14/849,551 dated Jan. 18, 2018, 10 pages.

Office Action for U.S. Appl. No. 15/047,344 dated Jun. 5, 2018, 43 pages.

Internation Search Report and Written Opinion dated Apr. 3, 2017 for International Application Serial No. PCT/US2017/1013885, 14 pages.

Afridi M. et al: "Transient heating study of microhotplates by using a high-speed thermal imaging system", 18th Annual IEEE Semiconductor Thermal Measurement and Management Symposium. Semi-Therm. Proceedings 2002. San Jose, CA, Mar. 2002; [IEEE Semiconductor Thermal Measurement and Management Symposium. Semi-Therm], New York, NY IEEE, US, Mar. 12, 2002 (Mar. 12, 2002), pp. 92-98, XP032155652.

ANSYS, "Thermal Solutions for 3-D IC, Packages and Systems", Jan. 1, 2013 (Jan. 1, 2013), XP055358498, Retrieved from the Internet: URL:http://resource.ansys.com/staticassets /ANSYS/ staticassets/resourcelibrary/techbrief/tb-thermal-solutions-for-3d-ic-pkg-and -sys.pdf [retrieved on Mar. 24, 2017] the whole document.

Office Action for U.S Appl. No. 16/038,499 dated Oct. 1, 2018, 22 pages.

Office Action dated Dec. 11, 2018 for U.S. Appl. No. 15/047,344, 27 pages.

Office Action dated Dec. 19, 2018 for U.S. Appl. No. 15/000,729, 30 pages.

Final Office Action for U.S. Appl. No. 14/849,551 dated Feb. 14, 2019, 25 pages.

Final Office Action for U.S. Appl. No. 16/038,499 dated Feb. 27, 2019, 23 pages.

Final Office Action received for U.S. Appl. No. 15/000,729 dated Apr. 5, 2019, 12 pages.

Non-Final Office Action for U.S. Appl. No. 16/038,499 dated Jun. 25, 2019, 15 pages.

Non-Final Office Action for U.S. Appl. No. 15/047,344 dated Jun. 27, 2019, 37 pages.

* cited by examiner

SUBSTANCE SENSING WITH TRACERS

TECHNICAL FIELD

The subject disclosure relates generally to sensors, e.g., substance sensing using tracers.

BACKGROUND

Electronic gas or chemical sensors can be used to sense gases, chemicals, scents, and/or odors. With regard to sensing or detecting gases, chemicals, scents, and/or odors, electronic gas or chemical sensors can operate differently than the human nose, and thus, can have different sensitivities to gases, chemicals, scents, and/or odors than the human nose.

The above-described description is merely intended to provide a contextual overview relating to antennas in wireless mobile systems, and is not intended to be exhaustive.

SUMMARY

The following presents a simplified summary of various aspects of the disclosed subject matter in order to provide a basic understanding of some aspects described herein. This summary is not an extensive overview of the disclosed subject matter. It is intended to neither identify key or critical elements of the disclosed subject matter nor delineate the scope of such aspects. Its sole purpose is to present some concepts of the disclosed subject matter in a simplified form as a prelude to the more detailed description that is presented later.

One or more embodiments, such as one or more devices, systems, methods, integrated circuits, and techniques disclosed herein, relate to sensing substances and controlling emission of substances. Disclosed herein is a system comprising a substance sensor component that senses an amount of a tracer substance being emitted with a substance. The system also comprises an emission management component that controls emission of the substance based at least in part on the amount of the tracer substance being emitted.

Also disclosed herein is a device that comprises a sensor component that detects a level of a tracer substance being emitted with a substance from the device. The device also comprises an emission management component that controls emission of the substance from the device based at least in part on the level of the tracer substance being emitted from the device.

Further disclosed herein is a method comprising sensing, by a system comprising a processor, an amount of a tracer substance being emitted with a substance. The method also comprises managing, by the system, emitting the substance based at least in part on the amount of the tracer substance being emitted.

The following description and the annexed drawings set forth in detail certain illustrative aspects of the disclosed subject matter. These aspects are indicative, however, of but a few of the various ways in which the principles of the disclosed subject matter may be employed, and the disclosed subject matter is intended to include all such aspects and their equivalents. Other advantages and distinctive features of the disclosed subject matter will become apparent from the following detailed description of the disclosed subject matter when considered in conjunction with the drawings.

DETAILED DESCRIPTION

Figure 1:
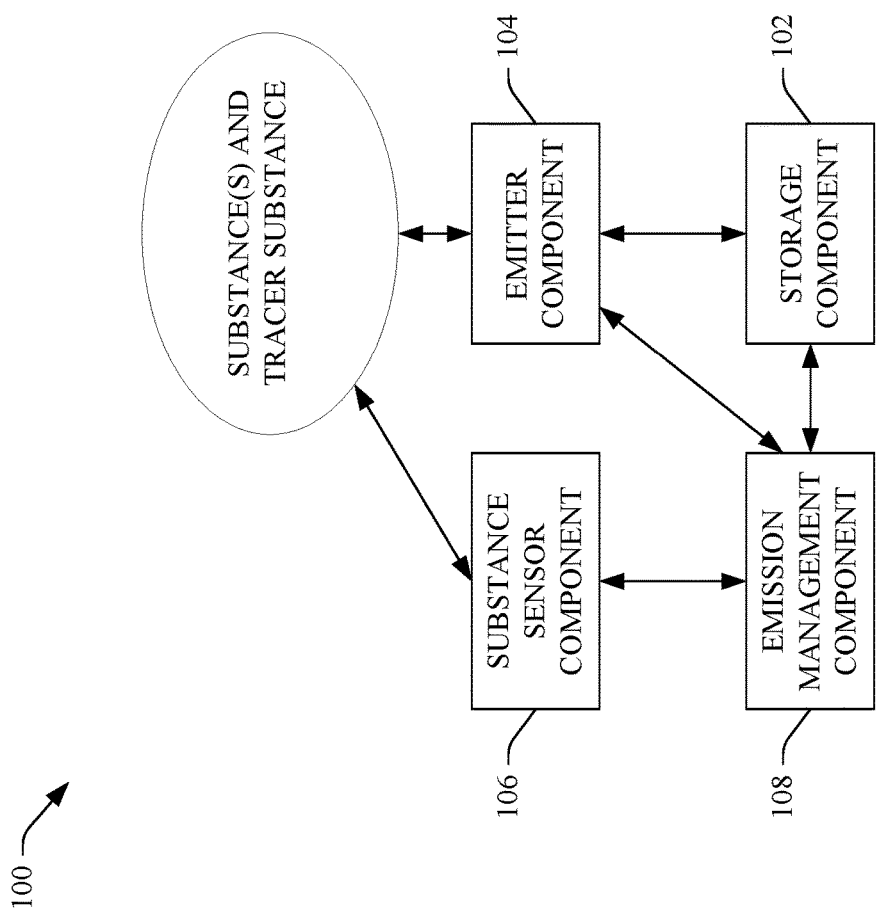
FIG. 1 illustrates a block diagram of an example system that can control an amount of a substance being emitted, in accordance with various aspects and embodiments of the disclosed subject matter.

The disclosed subject matter is described with reference to the drawings, wherein like reference numerals are used to refer to like elements throughout. In the following description, for purposes of explanation, numerous specific details are set forth in order to provide a thorough understanding of the various embodiments of the subject disclosure. It may be evident, however, that the disclosed subject matter may be practiced without these specific details. In other instances, well-known structures and devices are shown in block diagram form in order to facilitate describing the various embodiments herein.

Electronic gas or chemical sensors can be used to sense various substances, such as gases, chemicals, scents, and/or odors. With regard to sensing or detecting gases, chemicals, scents, and/or odors, electronic gas or chemical sensors can operate differently than the human nose, and thus, can have different sensitivities to gases, chemicals, scents, and/or odors than the human nose.

Many buildings and homes have air fresheners that emit an aromatic scent (e.g., a fragrance) into a room(s) to try to create a pleasant atmosphere. Often, when a person is subject to an aromatic scent for a significant period of time, the olfactory sensing of the person can become somewhat desensitized to the aromatic scene. As a result, the person may not realize when an air freshener is emitting too much aromatic scent into a room (e.g., to a point where the aromatic scent can be overwhelming or offensive to another person who has not been desensitized to the aromatic scent). This can result in an unpleasant experience for other people who are in the room, but who are not desensitized to the aromatic scent.

Also, while a certain amount of aromatic scent being emitted into a room can be desirable under certain environmental conditions (e.g., temperature, humidity, air pressure, and/or air flow), under different environmental conditions (e.g., after a change in environmental conditions), that certain amount of aromatic scent being emitted into the room may be less desirable or suitable.

There are some conventional devices, e.g., gas sensing equipment, such as optical absorption spectrometers or mass spectrometer/gas chromatography systems, that can be used to detect concentrations of certain types of gases. However, such conventional devices can be too large and too expensive to be used in a consumer electronics system or device.

To that end, systems, methods, devices, and techniques for controlling an amount of a substance (e.g., a scented or aromatic substance) being emitted (e.g., in a defined area) are presented. A substance(s) (e.g., gas, chemical, and/or scent (e.g., aromatic scent or fragrance)) can be mixed with a tracer substance in a known defined ratio of a first portion of the tracer substance to a second portion of the substance(s). The tracer substance can be safe, colorless, and/or odorless with respect to people as well as being safe with regard to other entities or things (e.g., animals, plants). During emission of the substance and the tracer substance, for example, in a defined area, a substance sensor component can sense or detect the tracer substance and/or the amount of the tracer substance being emitted (e.g., by an emitter component(s) of a system or a device). In some implementations, the substance sensor component can be configured to distinguish between the substance and the tracer substance, and to accurately detect and/or measure the amount of the tracer substance being emitted.

The substance sensor component can be associated with an emission management component, wherein the substance sensor component can communicate information relating to the sensing or detecting of the tracer substance to the emission management component. The emission management component can control the emission of the substance(s) based at least in part on the amount of the tracer substance sensed, detected, and/or measured during the emission of the substance(s) and the tracer substance.

In some implementations, a sensor component can comprise an environment sensor component as well as the substance sensor component. The environment sensor component can comprise one or more sensors (e.g., a temperature sensor, a humidity sensor, an air pressure sensor, and/or an air flow sensor) that can sense one or more different types of environmental conditions (e.g., temperature, humidity, air pressure, and/or air flow) in the defined area associated with the system or device. The emission management component can control emission of the substance in the defined area based at least in part on the tracer substance and the environmental conditions sensed, detected, and/or measured in the defined area.

These and other aspects of the disclosed subject matter are described with regard to the figures.

Turning to FIG. 1, illustrated is a block diagram of an example system 100 that can control an amount of a substance (e.g., a scented or aromatic substance) being emitted, in accordance with various aspects and embodiments of the disclosed subject matter. The system 100 can be, can comprise, or can be used in connection with one or more sensors, gyroscopes, accelerometers, or other components or devices. In some implementations, the system 100 can be, can comprise, or can be used in connection with one or more micro-electromechanical systems (MEMS) or semiconductor sensors, gyroscopes, or accelerometers.

The system 100 can comprise a storage component 102 that can store one or more substances that can be emitted by the system 100, for example, into a defined area (e.g., an indoor area inside of a home or other building, a defined or confined region, an outdoor area). The one or more substances can be or can comprise, for example, a gas(es), a liquid (e.g., a liquid in mist form), a chemical(s), and/or a scent(s) (e.g., aromatic scent(s) or fragrance(s)). For instance, the system 100 can be employed to emit a substance(s), which can be an air freshener or fragrance, into a room.

The system 100 also can include an emitter component 104 that can be associated with (e.g., connected to) the storage component 102. The emitter component 104 can access the storage component 102 and can receive, retrieve, or obtain the one or more substances from the storage component 102. The emitter component 104 can emit the one or more substances from the emitter component 104, for example, into the defined area (e.g., into the air in the defined area). It is to be appreciated and understood that, as disclosed herein, a substance being emitted can be one type of substance (e.g., one type of aromatic scent) or can comprise a combination of substances (e.g., a combination of different types of aromatic scents comprising at least a first aromatic scent and a second aromatic scent).

The system 100 further can comprise a substance sensor component 106 that can be employed to sense or detect, and/or measure an amount of, a tracer substance (e.g., tracer gas or chemical) being emitted with a substance or a combination of substances (e.g., two or more substances comprising at least the substance and a second substance) by the emitter component 104, for example, in the defined area in proximity to the substance sensor component 106. The substance sensor component 106 can monitor all or a portion of the defined area in proximity to the substance sensor component 106 to facilitate sensing, detecting, or measuring the tracer substance.

In some implementations, the tracer substance can be mixed (e.g., pre-mixed) or otherwise associated with the substance or combination of substances (e.g., two or more substances comprising at least the substance and a second substance) and stored in the storage component 102 (e.g., stored in the same chamber of the storage component 102). In other implementations, the tracer substance can be stored in another chamber (e.g., reservoir) of the storage component 102 that can be separate from the chamber(s) of the storage component 102 that is storing the substance or combination of substances. In such instance, the emitter component 104 can mix or associate the tracer substance with the substance or combination of substances in respective desired portions (e.g., in accordance with a defined ratio of the tracer substance to the substance(s)) as the emitter component 104 is emitting the tracer substance and substance or combination of substances.

The amount of the tracer substance mixed with the substance can be a desired amount relative to the amount of the substance, in accordance with defined substance criteria. For example, as the tracer substance is being used to facilitate tracing the amount of the substance being emitted by the emitter component 104, the amount of tracer substance can be substantially smaller than the amount of the substance (e.g., less than 1% tracer substance to more than 99% substance, 1% tracer substance to 99% substance, more than 1% tracer substance to less than 99% substance). The tracer substance can be safe, colorless, and/or odorless with respect to people as well as being safe with regard to other entities or things (e.g., animals, plants). For example, the tracer substance can be a type of substance that is determined to be odorless with respect to an olfactory sense of people (or at least substantially all people), safe with respect to people, and/or colorless with respect to people, in accordance with the defined substance criteria that relates to odor, safety, and/or color.

In certain implementations, the substance sensor component 106 can be or can comprise one or more electronic gas or chemical sensors that can be used to facilitate monitoring all or a desired portion of the defined area in proximity to the substance sensor component 106 and sensing, detecting, or measuring the tracer gas by the substance sensor component 106. For example, the substance sensor component 106 can be or can comprise a metal oxide-based gas or chemical sensor (e.g., metal oxide semiconductor (MOS) gas or chemical sensor). In some implementations, the substance sensor component 106 can be or can comprise a sensor (e.g., gas or chemical sensor) configured using MEMS technology (e.g., a MEMS sensor). The system 100, including the substance sensor component 106, can be relatively small in size, low cost, and low power (e.g., can consume a low amount of power when used).

The one or more electronic gas or chemical sensors of the substance sensor component 106 can be constructed, fabricated, and/or configured using one or more desired techniques, systems, methods, or processes. For example, the one or more electronic gas or chemical sensors of the substance sensor component 106 can be constructed, fabricated, and/or configured using one or more desired techniques, systems, methods, or processes, such as disclosed in U.S. patent application Ser. No. 14/849,551, filed on Sep. 9, 2015, and entitled "GAS SENSOR PLATFORM AND THE METHOD OF MAKING SAME," U.S. patent application Ser. No. 15/000,729, filed on Jan. 19, 2016, and entitled "CMOS INTEGRATED MICROHEATER FOR A GAS SENSOR DEVICE," and U.S. patent application Ser. No. 15/047,344, filed on Feb. 18, 2016, and entitled "GAS SENSING MATERIAL FOR A GAS SENSOR DEVICE," the entireties of which applications are hereby incorporated herein by reference.

The molecules of the substance(s) being emitted by the emitter component 104 may be complex and may make it relatively difficult to detect the molecules of the substance(s) with desirable selectivity. The tracer substance can be determined and selected (e.g., relative to the substance(s) with which it will be associated) such that it can be relatively easier for the tracer substance to be sensed, detected, or measured by the substance sensor component 106 (e.g., as compared to sensing of the substance(s)).

To facilitate desirable ability of the substance sensor component 106 (e.g., the one or more electronic gas or chemical sensors of the substance sensor component 106) to accurately sense, detect, or measure (e.g., selectively) the tracer substance and/or differentiate between the tracer substance and the substance(s), the substance sensor component 106 (e.g., the one or more electronic gas or chemical sensors) can be designed, constructed, or configured to be able to accurately sense, detect, and/or measure the tracer substance (e.g., molecules of the tracer substance) without the substance(s) (e.g., molecules of the substance(s)) with which the tracer substance is mixed interfering with the sensing, detecting, and/or measuring of the tracer substance by the substance sensor component 106. To facilitate accurate sensing, detecting, or measuring of the tracer substance, the substance sensor component 106 can comprise a set of characteristics (e.g., attributes, features, properties) that can be configured (e.g., set, selected, or tailored) to enable the substance sensor component 106 to sense, detect, measure, or be selective to (e.g., sensitive only to) the tracer substance without sensing, without being selective to, or without interference by the substance(s) (e.g., aromatic scent(s) or fragrance(s)) with which the tracer substance is mixed and/or by being able to differentiate between the tracer substance and the substance(s).

With respect to different substances (e.g., aromatic scents or fragrances) that can be emitted by the emitter component 104, a desirable tracer substance (e.g., a suitable, acceptable, optimal) tracer substance can be identified and used with regard to a respective substance or set (e.g., group or type) of substances, based at least in part on the respective characteristics (e.g., the respective chemical properties) of the respective types of tracer substances and the respective characteristics (e.g., the respective chemical properties) of the respective types of substances. For instance, a first type of tracer substance can be desirable for use with a first substance or a first set of substances, and a second type of tracer substance can be desirable for use with a second substance or a second set of substances, in connection with controlling the emission of the first substance or the first set of substances and the second substance or the second set of substances.

In response to sensing, detecting, or measuring (e.g., measuring the amount, level, or concentration) of the tracer substance, the substance sensor component 106 can generate information (e.g., tracer substance related information) that can be used to facilitate controlling the emission of the tracer substance and the substance(s) with which the tracer substance is associated (e.g., mixed). The information can comprise measurement information can specify the amount of the tracer substance, or can comprise other information that can be used to measure or determine the amount of the tracer substance, sensed or detected by the substance sensor component 106.

The system 100 also can comprise an emission management component 108 that can be associated with (e.g., connected to) the substance sensor component 106 and the emitter component 104. The emission management component 108 can monitor the substance sensor component 106 and can receive the information (e.g., tracer substance related information) from the substance sensor component 106. The emission management component 108 can analyze the information received from the substance sensor component 106. The emission management component 108 can determine the amount (e.g., amount, level, or concentration) of the tracer gas that is being emitted with the substance(s) based at least in part on the results of the analysis of the information (e.g., tracer substance related information).

The emission management component 108 can know a defined ratio of a first portion of the tracer substance to a second portion of the substance(s) (e.g., the substance, or a combination of two or more substances comprising at least the substance and a second substance) for the combination of the tracer substance and the substance(s) being emitted by the emitter component 104. For instance, the amount of the tracer substance can be added to the substance(s), in accordance with the defined ratio, to facilitate enabling the amount (e.g., amount, level, concentration) of the tracer substance to be correlated with the amount of the substance(s) the people in or associated with the defined area can be experiencing. Accordingly, the emission management component 108 can determine the amount of the substance(s) being emitted by the emitter component 104 based at least in part on the amount of the tracer gas measured to be emitted by the emitter component 104 and the defined ratio. For example, if the first portion of the tracer substance is 1 part of the tracer substance, and the second portion of the substance is 99 parts of the substance(s), the defined ratio can be 1 (of the tracer substance) to 99 (of the substance(s)), and the emission management component 108 can determine the amount of the substance(s) being emitted based at least in part on the amount of the tracer gas being emitted and the defined ratio of 1 to 99.

The emission management component 108 also can know a desirable amount of the substance(s) to be emitted by the emitter component 104 to the defined area based at least in part on the type(s) of substance(s) being emitted and/or the conditions (e.g., environmental conditions, expected range of environmental conditions, conditions of a closed indoor area, conditions of an open or semi-open area) associated with the defined area. For instance, a desirable amount of the substance(s) to be emitted by the emitter component 104 to the defined area can be determined by the emission management component 108 such that the amount of the substance(s) can be observed to be or identified as being desirable (e.g., acceptable, suitable, enjoyable, optimal) to people (e.g., at least a desirable percentage (e.g., most) people) who may be expected to be in the defined area and to perceive or experience (e.g., sense or smell) the substance(s), in accordance with the defined substance criteria.

In some implementations, if the emission management component 108 does not have information regarding the actual current environmental conditions of the defined area (e.g., due to no information relating to environmental conditions of the defined area being available or due to no sensing of the environmental conditions being performed), the desirable amount of the substance(s) to be emitted by the emitter component 104 to the defined area can be determined (e.g., by the emission management component 108) based at least in part on an expected or average range of environmental conditions for the defined area. For example, a particular defined area (e.g., a room in a building) may typically be maintained at temperatures ranging from 68° to 72° Fahrenheit (F) and humidity levels ranging from 40% to 60% humidity. The desirable amount of the substance(s) to be emitted to the defined area can be determined (e.g., by the emission management component 108 or another component) based at least in part on the typical temperature range of 68° to 72° F. (or average temperature of, e.g., 70° F.) and the typical humidity level range of 40% to 60% humidity (or an average humidity level of, e.g., 50%).

The emission management component 108 can control and/or adjust the amount of emission of the substance(s) by the emitter component 104 based at least in part on the amount of the tracer substance being emitted by the emitter component 104 and the defined ratio, in accordance with the defined substance criteria, which can relate to or indicate the desirable amount of the substance(s) to be emitted by the emitter component 104 to the defined area. For example, the emission management component 108 can control the amount of emission of the substance(s) by the emitter component 104 to increase the amount of emission of the substance(s), in response to determining that the amount of the substance(s) being emitted is too low, based at least in part on the amount of the tracer substance being emitted and the defined ratio, in accordance with the defined substance criteria. Alternatively, the emission management component 108 can control the amount of emission of the substance(s) by the emitter component 104 to decrease (or maintain at its current level) the amount of emission of the substance(s), in response to determining that the amount of the substance(s) being emitted is too high (or is appropriate at its current level), based at least in part on the amount of the tracer substance being emitted and the defined ratio, in accordance with the defined substance criteria. The emission management component 108 can thereby efficiently control the amount of the substance(s) emitted, by the emitter component 104, to the defined area to desirably control the experience of the substance(s) by people in or associated with the defined area and to release more or less of the substance(s) as is desirable, in accordance with the defined substance criteria.

In this way, the system 100 can comprise a feedback loop (e.g., via sensing and measuring the amount of tracer gas being emitted with the substance(s), wherein the information received via the feedback loop can be used to facilitate controlling the emission of the substance(s) (and the tracer substance)) that can facilitate a desirable experience (e.g., olfactory experience) for people who are or may be in or in proximity to the defined area. This feedback loop can facilitate enabling the substance sensor component 106 and the emission management component 108 to account for different diffusion rates of the substance or various different substances in the defined area (e.g., with respect to people in the defined area) depending on different conditions associated with the defined area, wherein the conditions can comprise, for example, environmental conditions (e.g., temperature, humidity, air pressure, and/or air flow or wind speed) associated with the defined area. For example, different types of substances can diffuse differently in the air in a defined area under the same conditions (e.g., environmental conditions). Also, a particular substance can diffuse in the air in the defined area differently under different conditions (e.g., different environmental conditions), for example, in response to a change in conditions.

With further reference to the substance sensor component, 106, in some implementations, the one or more sensors of the substance sensor component 106 can be contained in a same device with other components (e.g., storage component 102, emitter component 104, emission management component 108) of the system 100. In other implementations, one or more of the sensors of the substance sensor component 106 can be located remotely (e.g., outside of the device) from the other components of the system 100, wherein such remote sensor(s) can communicate (e.g., transmit or receive information) with the other components (e.g., emission management component 108) of the system 100 via a wired or wireless communication connection.

Figure 2:
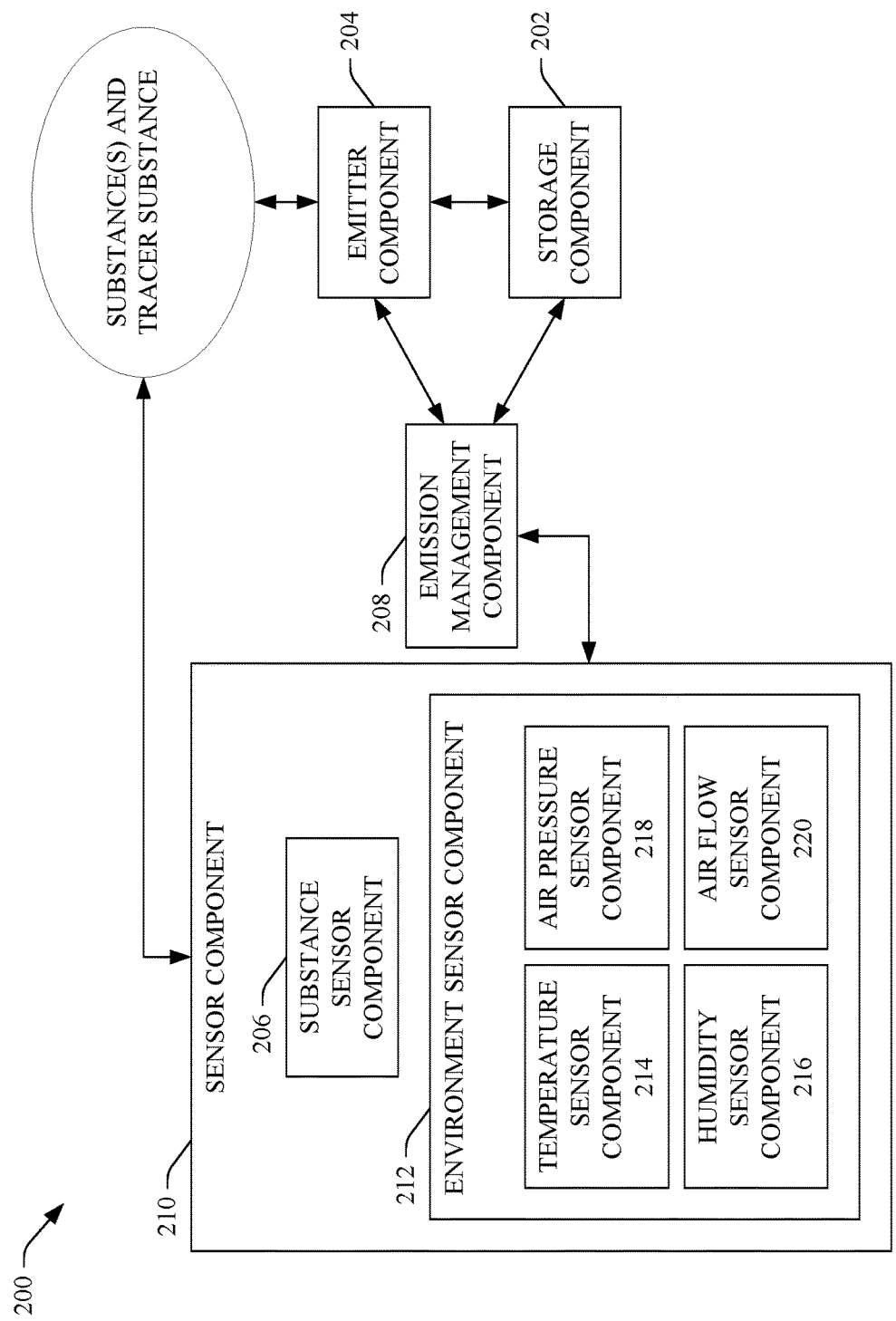
FIG. 2 depicts a block diagram of an example system that can control an amount of a substance being emitted based at least in part on environmental conditions, in accordance with various aspects and embodiments of the disclosed subject matter.

FIG. 2 depicts a block diagram of an example system 200 that can control an amount of a substance being emitted based at least in part on environmental conditions, in accordance with various aspects and embodiments of the disclosed subject matter. The system 200 can be, can comprise, or can be used in connection with one or more sensors, gyroscopes, accelerometers, or other components or devices (e.g., MEMS or semiconductor sensors, gyroscopes, accelerometers, or other components or devices). The system 200 can comprise a storage component 202, emitter component 204, substance sensor component 206, and an emission management component 208, that, respectively, can be the same as or similar to, and/or can comprise the same or similar features or functionalities as, respective components (e.g., respectively named components), as more fully disclosed herein.

The system 200 also can comprise a sensor component 210 that can comprise the substance sensor component 206 and an environment sensor component 212. The sensor component 210 can sense various types of characteristics (e.g., a tracer substance(s), environmental conditions) associated with, for example, a defined area.

The substance sensor component 206 can monitor all or a portion of, for example, the defined area in proximity to the substance sensor component 206 to facilitate sensing, detecting, or measuring a tracer substance being emitted with a substance(s) (e.g., the substance, or a combination of substances comprising at least the substance and a second substance) by the emitter component 104, for example, in the defined area in proximity to the substance sensor component 206. The substance sensor component 206 can sense or detect, and/or measure an amount of, the tracer substance and can generate information relating to the sensing, detecting, and/or measuring of the tracer substance. The substance sensor component 206 can communicate such information relating to the sensing, detecting, and/or measuring of the tracer substance to the emission management component 208.

The environment sensor component 212 can comprise one or more sensors that can be employed to facilitate sensing, detecting, and/or measuring one or more types of environmental conditions associated with the defined area in which the substance(s) (e.g., the substance or the combination of substances) and the tracer substance is being emitted by the emitter component 204. In accordance with various implementations, the environment sensor component 212 can comprise a temperature sensor component 214, a humidity sensor component 216, an air pressure sensor component 218, and/or an air flow sensor component 220 that can facilitate sensing, detecting, or measuring respective environmental conditions (e.g., temperature, humidity, air pressure, air flow or wind speed) associated with the defined area. For instance, the temperature sensor component 214 can sense, detect, or measure, and can generate information (e.g., temperature information) relating to, the temperature in or associated with the defined area. The humidity sensor component 216 can sense, detect, or measure, and can generate information (e.g., humidity information) relating to, the level of humidity in or associated with the defined area. The air pressure sensor component 218 can sense, detect, or measure, and can generate information (e.g., air pressure information) relating to, the level of air pressure in or associated with the defined area. The air flow sensor component 220 can sense, detect, or measure, and can generate information (e.g., air flow information) relating to, the amount (e.g., level, rate) of the air flow or wind speed in or associated with the defined area.

The environment sensor component 212 can be associated with (e.g., connected to) the emission management component 208. The emission management component 208 can receive the respective information (e.g., temperature information, humidity information, air pressure information, and/or air flow information) from the temperature sensor component 214, the humidity sensor component 216, the air pressure sensor component 218, and/or the air flow sensor component 220.

The emission management component 208 can analyze the information relating to the sensing, detecting, and/or measuring of the tracer substance and the information relating to the environmental conditions (e.g., temperature information, humidity information, air pressure information, and/or air flow information). The emission management component 208 also can know a defined ratio of the tracer substance and the substance(s) being emitted by the emitter component 204. For instance, with regard to the mixture of the tracer substance and the substance(s), the emission management component 208 can know the defined ratio of the first portion of the tracer substance to the second portion of the substance(s) being emitted.

Based at least in part on the results of the analysis the information relating to the tracer substance and the defined ratio, the emission management component 208 can determine the amount of the substance(s) that is being emitted in the defined area by the emitter component 204. Based at least in part on the results of the analysis the information relating to the environmental conditions, the emission management component 208 can determine or identify the respective environmental conditions (e.g., temperature, humidity level, air pressure level, and/or air flow level or wind speed) in the defined area.

The emission management component 208 can determine a desired (e.g., appropriate, suitable, acceptable, or optimal) amount of the substance(s) that is to be emitted to the defined area based at least in part on the respective environmental conditions in the defined area and the defined substance criteria, which can identify or indicate the desired amount of the substance(s) that is to be emitted to the defined area under particular environmental conditions. For instance, the defined substance criteria can indicate that, under a first set of environmental conditions, a first amount of the substance(s) is to be emitted to the defined area, under a second set of environmental conditions, a second amount of the substance(s) is to be emitted to the defined area, under a third set of environmental conditions, a third amount of the substance(s) is to be emitted to the defined area, etc. The environmental conditions (e.g., the first set, second set, or third set of environmental conditions) can be determined (e.g., by the emission management component 208) based at least in part on feedback information (e.g., information relating to sensed environmental conditions) received from the environment sensor component 212.

The emission management component 208 can compare the amount of the substance(s) determined to be emitted in the defined area with the desired amount of the substance(s) that should be emitted in the defined area to facilitate determining an adjustment (if any) that is to be made to the amount of the substance(s) being emitted in the defined area. Based on the results of the comparison of the amount of the substance(s) being emitted to the defined area with the desired amount of the substance(s) that should be emitted to the defined area, the emission management component 208 can determine whether there is a difference between the amount of the substance(s) being emitted and the desired amount of the substance(s) that should be emitted to the defined area, in accordance the defined substance criteria.

If the emission management component 208 determines that the amount of the substance(s) being emitted to the defined area is too high, the emission management component 208 can adjust the amount of the substance(s) being emitted to the defined area to reduce (e.g., decrease) the amount of the substance(s) being emitted to the desired amount. If the emission management component 208 determines that the amount of the substance(s) being emitted to the defined area is too low, the emission management component 208 can adjust the amount of the substance(s) being emitted to the defined area to increase the amount of the substance(s) being emitted to the desired amount. If the emission management component 208 determines that the amount of the substance(s) being emitted to the defined area is at the desired (e.g., appropriate, suitable, acceptable, or optimal) level, the emission management component 208 can determine that no adjustment is to be made to the amount of the substance(s) being emitted to the defined area.

The emission management component 208 can generate instructions and send the instructions to the emitter component 204 to facilitate controlling operation of the emitter component 204, or can otherwise control operation of the emitter component 204, to have the emitter component 204 adjust the amount of the substance(s) being emitted to the defined area to the desired amount of the substance(s) (e.g., if it is determined that an adjustment is to be made to increase or decrease the amount of the substance(s)), or maintain the amount of the substance(s) being emitted to the defined area at the desired amount (e.g., if it is determined that no adjustment is to be made). The emission management component 208 can facilitate making adjustments to the amount of the substance(s) being emitted to the defined area periodically (e.g., at regular or irregular time intervals) and/or dynamically in response to a detected change in conditions (e.g., change in the environmental conditions in the defined area, or change in the substance(s) being emitted).

Figure 3:
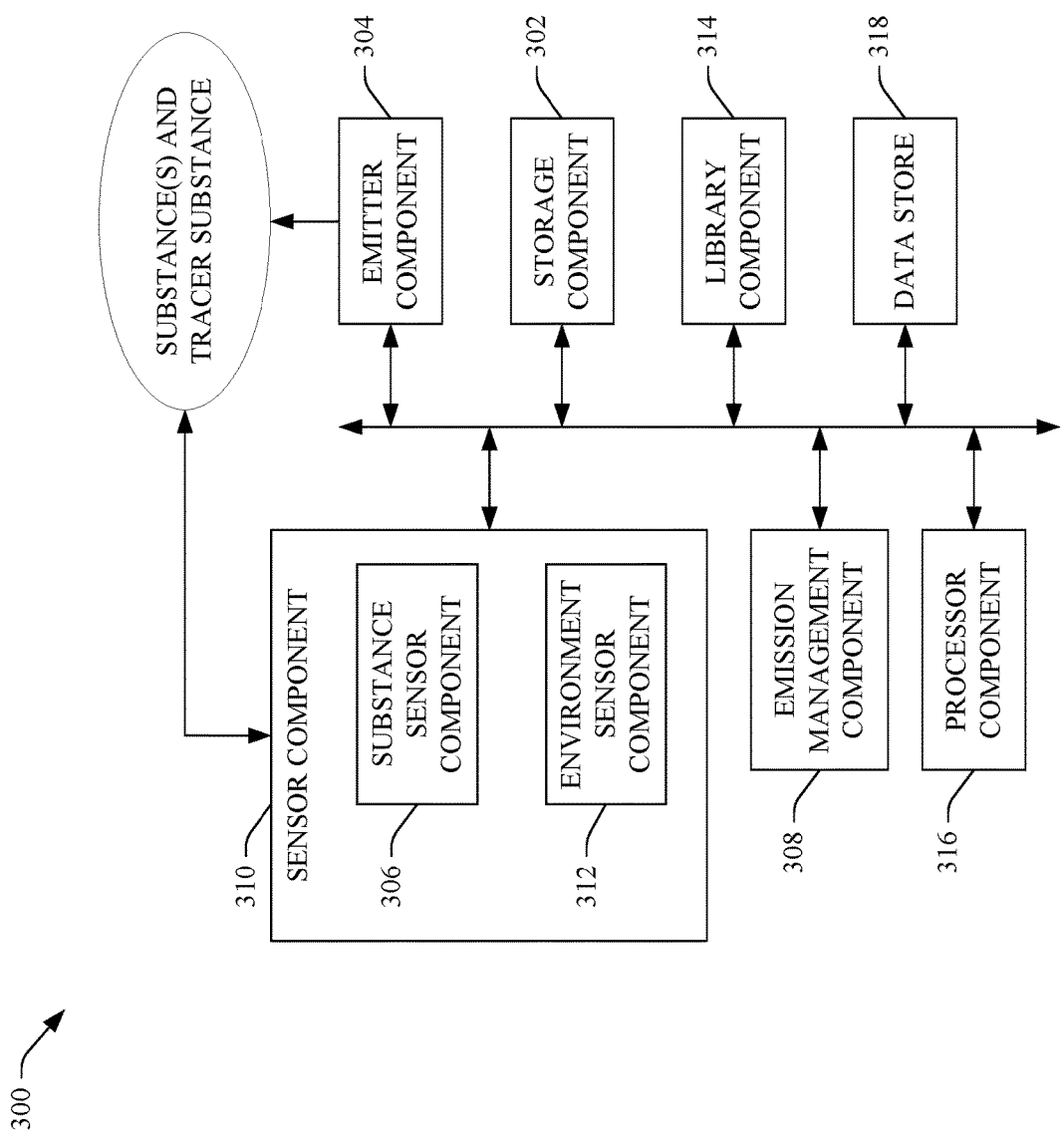
FIG. 3 presents a block diagram of another example system that can control an amount of a substance being emitted, in accordance with various aspects and embodiments of the disclosed subject matter.

FIG. 3 presents a block diagram of another example system 300 that can control an amount of a substance being emitted, in accordance with various aspects and embodiments of the disclosed subject matter. The system 300 can be, can comprise, or can be used in connection with one or more sensors, gyroscopes, accelerometers, or other components or devices (e.g., MEMS or semiconductor sensors, gyroscopes, accelerometers, or other components or devices). The system 300 can comprise a storage component 302, an emitter component 304, a substance sensor component 306, an emission management component 308, a sensor component 310, and an environment sensor component 312 that, respectively, can be the same as or similar to, and/or can comprise the same or similar features or functionalities as, respective components (e.g., respectively named components), as more fully disclosed herein.

The system 300 can include a library component 314 that can comprise respective sets of information relating to respective tracer substances, respective substance sensor components, respective adjustments to the respective substance sensor components, respective substances, respective defined ratios of respective portions of the respective tracer substances to respective other portions of the respective substances, and/or respective mappings associated with the respective tracer substances. The emission management component 308 or another component(s) can generate such information of the library component 314. The emission management component 308 or another component(s) also can update such information of the library component 314 when there is a change to such information (e.g., a change to an item(s) of information).

In some implementations, the emission management component 308, the library component 314, or another component(s) can generate a mapping of one item of information to at least one other item of information of the library component 314, wherein the mapping can be used by the emission management component 308 to facilitate controlling emission of the substance (and the tracer substance) by the emitter component 304. For instance, the emission management component 308, the library component 314, or another component(s) can generate a mapping of a substance to a tracer substance and a defined ratio of a first portion of the tracer substance to a second portion of the substance. When the substance is selected (e.g., by the emission management component 308, another component, or a user) for emission to the defined area, the emission management component 308 can access the mapping of the substance to the tracer substance and the defined ratio stored in the library component 314 to identify the tracer substance being used with the substance and/or to identify the defined ratio, wherein the emission management component 308 can use the defined ratio to facilitate controlling the emission of the substance to the defined area, as more full disclosed herein.

As another example, the emission management component 308, the library component 314, or another component(s) can generate a mapping of respective adjustments to a substance sensor component (e.g., 306) to respective substances and respective tracer substances. With respect to a particular substance and a particular tracer substance being used by the system 300, the emission management component 308 can access the mapping of respective adjustments to the substance sensor component (e.g., 306) to respective substances and respective tracer substances stored in the library component 314. Based at least in part on an analysis of such mapping, the emission management component 308 can identify or determine an adjustment(s) to be made to or setting(s) (e.g., parameter value(s), such as a temperature parameter value) of the substance sensor component (e.g., 306) based at least in part on the particular substance and the particular tracer substance being used. The emission management component 308 can facilitate adjusting or selecting a setting(s) (e.g., a parameter value(s)) on the substance sensor component (e.g., 306).

The system 300 also can comprise a processor component 316 that can comprise or or more of a processor(s), a microprocessor(s), a controller(s), a microcontroller(s), and/or another type of processing device that can perform or facilitate performing various functions to facilitate controlling operations of the system 300, including controlling emission of a substance to the defined area. The processor component 316 can be associated with (e.g., connected to) the emitter component 304 to facilitate controlling operation of the emitter component 304 with respect to emitting a substance to the defined area. The processor component 316 can be associated with the substance sensor component 306 to facilitate controlling operation of the substance sensor component 306 with respect to sensing a tracer substance being emitted with a substance to the defined area and with respect to the substance sensor component 306 communicating information relating to sensing a tracer substance or measuring the amount of a tracer substance being emitted to the emission management component 308, the processor component 316, or a data store 318.

The processor component 316 also can be associated with the emission management component 308 to facilitate controlling operation of the emission management component 308 and/or facilitate performing operations in conjunction with the emission management component 308 with respect to controlling emission of a substance (and a tracer substance) to the defined area. The processor component 316 can be associated with the environment sensor component 312 to facilitate controlling operation of the environment sensor component 312 with respect to sensing environmental conditions associated with the defined area and with respect to the environment sensor component 312 communicating information relating to the environmental conditions to the emission management component 308, the processor component 316, or a data store 318.

The one or more processors, microprocessors, controllers, and/or microcontrollers of the processor component 316 can process data, such as information relating to sensing or measuring a tracer substance being emitted to a defined area associated with the system 300, sensing or measuring environmental conditions associated with the defined area, determining an amount of a tracer substance being emitted to the defined area, determining an amount of a substance to be emitted to the defined area, a defined ratio of a tracer substance to a substance, mappings, policies, defined substance criteria, algorithms (e.g., a defined substance emission control algorithm), protocols, interfaces, tools, and/or other information, to facilitate operation of the system 300, as more fully disclosed herein, control data flow between the components (e.g., storage component 302, emitter component 304, substance sensor component 306, emission management component 308, ...) of the system 300, and/or control data flow between the system 300 and other components (e.g., a communication network, a server or other communication device, a cloud, ...) associated with the system 300.

The data store 318 can store data structures (e.g., user data, metadata), code structure(s) (e.g., modules, objects, hashes, classes, procedures) or instructions, information relating to sensing or measuring a tracer substance being emitted to a defined area associated with the system 300, sensing or measuring environmental conditions associated with the defined area, determining an amount of a tracer substance being emitted to the defined area, determining an amount of a substance to be emitted to the defined area, a defined ratio of a tracer substance to a substance, mappings, policies, defined substance criteria, algorithms, protocols, interfaces, tools, and/or other information, to facilitate controlling operations associated with the system 300. In an aspect, the processor component 316 can be functionally coupled (e.g., through a memory bus) to the data store 318 in order to store and retrieve information desired to operate and/or confer functionality, at least in part, to storage component 302, emitter component 304, substance sensor component 306, emission management component 308, sensor component 310, etc., and/or substantially any other operational aspects of the system 300.

Figure 4:
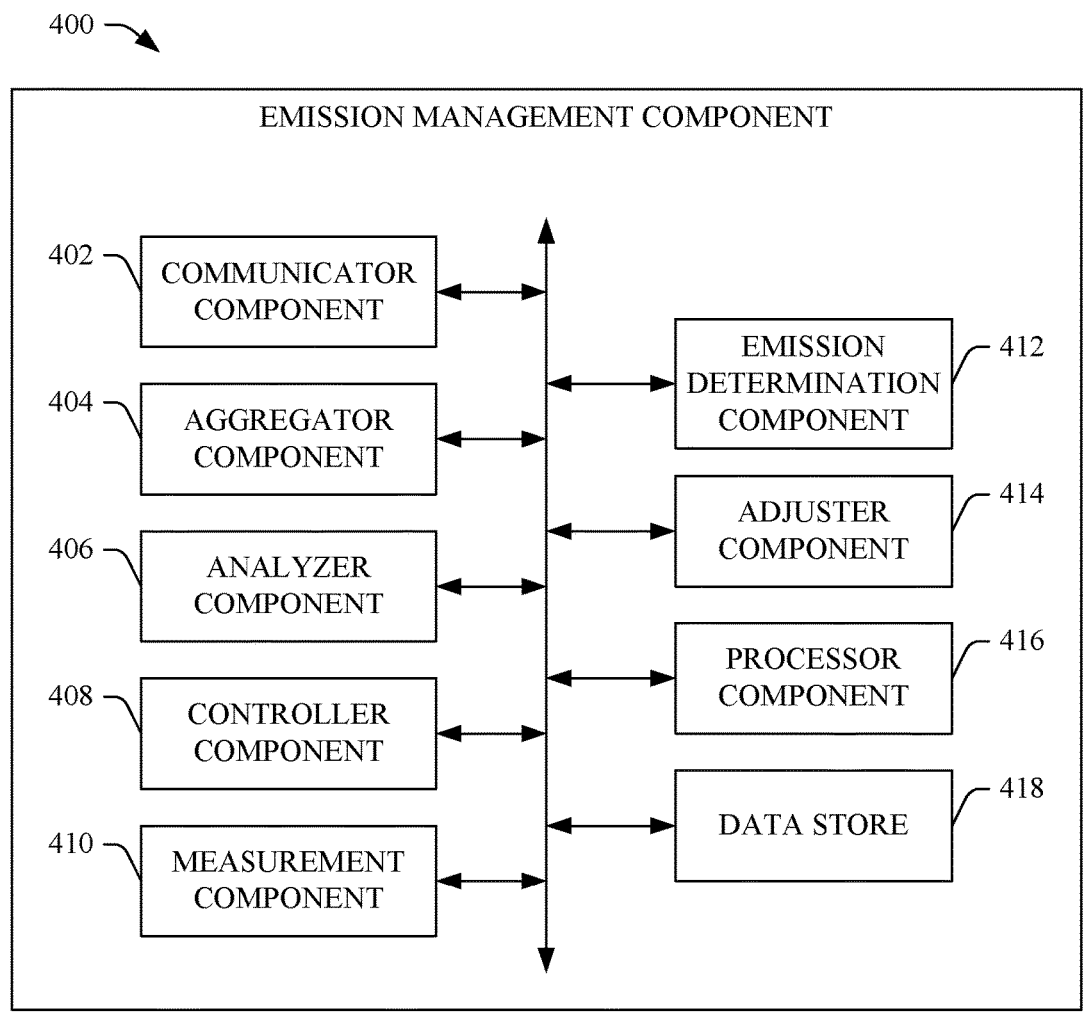
FIG. 4 illustrates a block diagram of an example emission management component that can facilitate controlling an amount of a substance being emitted, in accordance with various aspects and embodiments of the disclosed subject matter.

FIG. 4 illustrates a block diagram of an example emission management component 400 that can facilitate controlling an amount of a substance being emitted, in accordance with various aspects and embodiments of the disclosed subject matter. The emission management component 400 can comprise a communicator component 402, an aggregator component 404, an analyzer component 406, a controller component 408, a measurement component 410, an emission determination component 412, and an adjuster component 414.

The communicator component 402 can transmit or receive information to or from other components (e.g., sensor component, emitter component, remote device, ...) associated with the emission management component 400. For example, the communicator component 402 can receive information relating to emission of a tracer substance from a sensor substance component and/or can receive information relating environment conditions from an environment substance component. As another example, the communicator component 402 also can transmit information (e.g., instructions) relating to controlling emission of a substance (and a tracer substance) by the emitter component to the emitter component. The communicator component 402 can transmit or receive information to or from the other components via a wired or wireless connection using a desired wired or wireless communication technology or protocol.

The aggregator component 404 can aggregate data received (e.g., obtained) from various components, devices, or entities (e.g., a sensor component, an emitter component, a storage component, an application, a communication device, a processor, a data store, a user, etc.). The aggregator component 404 can correlate respective items of data based at least in part on type of data (e.g., data related a substance, data related to a tracer substance, data related to environmental conditions, measurement data, data related to a defined ratio, metadata, etc.), source (e.g., substance sensor component, environment sensor component, library component, ...) of the data, time or date an item of data was generated or received, etc., to facilitate analyzing of the data by the analyzer component 406. For example, the aggregator component 404 can aggregate items of data relating to a substance being emitted to a defined area, a tracer substance being emitted with the substance (e.g., an amount of the tracer substance determined to be emitted), and a defined ratio relating to the tracer substance and the substance to facilitate determining the amount of the substance being emitted to the defined area and controlling emission of the substance to the defined area.

The analyzer component 406 can analyze data to facilitate determining the amount of the tracer substance being emitted to the defined area, determining the amount of the substance being emitted to the defined area, determining environmental conditions of the defined area, determining whether an adjustment is to be made to the amount of the substance being emitted to the defined, and/or controlling emission of the substance to the defined area, etc., based at least in part on the data analysis. For example, the analyzer component 406 can analyze information received from the substance sensor component, the environment sensor component, and/or another component(s) to facilitate determining the amount of the tracer substance being emitted to the defined area, determining the amount of the substance being emitted to the defined area, determining environmental conditions of the defined area, and/or determining a desired amount of the substance that is to be emitted to the defined area. Based on analysis, the emission management component 400 can determine whether an adjustment is to be made to the amount of the substance being emitted to the defined area and can facilitate controlling emission of the substance to the defined area.

The controller component 408 can control operations relating to processing data, determining an amount of a tracer substance being emitted to a defined area, determining an amount of a substance being emitted to the defined area, determining environmental conditions of the defined area, determining a desired amount of the substance that is to be emitted to the defined area, determining whether an adjustment is to be made to the amount of the substance being emitted to the defined area, controlling emission of the substance to the defined area, and/or performing other operations in connection with the system (e.g., substance emission system). The controller component 408 can facilitate controlling operations being performed by various components of the emission management component 400, controlling data flow between various components of the emission management component 400, controlling data flow between the emission management component 400 and other components or systems associated with the emission management component 400, etc.

The measurement component 410 can determine or measure an amount of a tracer substance sensed by the substance sensor component based at least in part on information derived or obtained from sensing of the tracer substance emitted to the defined area by the substance sensor component. The measurement component 410 also can determine or measure respective amounts, levels, or values of respective environmental conditions (e.g., temperature, humidity, air pressure, and/or air flow) based at least in part on information derived or obtained from sensing of the respective environmental conditions of the defined area by the respective sensors (e.g., temperature sensor component, humidity sensor component, air pressure sensor component, air flow sensor component) of the environmental sensor component.

The emission determination component 412 can determine whether an adjustment is to be made, and determine an amount of an adjustment (if any) to be made, to the amount of the substance being emitted to a defined area to facilitate controlling emission of the substance to the defined area, based at least in part on the results of the analysis of the information relating to a tracer substance sensed in the defined area, information relating to environmental conditions of the defined area, and/or a defined ratio of a first portion of the tracer substance to a second portion of the substance being emitted to the defined area, in accordance with the defined substance criteria, as more fully disclosed herein. The adjuster component 414 can adjust an amount of a substance being emitted to a defined area, in response to the emission determination component 412 determining that an adjustment to the amount of the substance being emitted is to be made and in accordance with the amount of the adjustment to be made to the amount of the substance to be emitted to the defined area, as determined by the emission determination component 412. For instance, the adjuster component 414 can facilitate generating or communicating (e.g., via the controller component 408 and/or the communicator component 402) instructions to the emitter component to instruct the emitter component to adjust the amount of the emission of the substance in accordance with the instructions, or the adjuster component 414 can otherwise facilitate controlling operation of the emitter component to have the emitter component adjust the amount of emission of the substance to the defined area, in accordance with the amount of the adjustment to be made to the amount of the substance to be emitted to the defined area.

In some implementations, the adjuster component 414 also can be employed to adjust a characteristic, such as a parameter (e.g., temperature parameter), of a substance sensor component, for example, in response to a change in the substance or the tracer substance being emitted to the defined area. The adjuster component 414 further can adjust a characteristic (e.g., parameter, attribute) of one or more sensors of the environment sensor component, in response to a change in the substance or the tracer substance being emitted to the defined area or a change of environment or location in which the system or device (e.g., emission control system or emission control device) is being used.

The processor component 416 can work in conjunction with the other components (e.g., communicator component 402, aggregator component 404, analyzer component 406, controller component 408, measurement component 410, emission determination component 412, adjuster component 414, . . . ) to facilitate performing the various functions of the emission management component 400. The processor component 416 can employ one or more processors, microprocessors, or controllers that can process data, such as information relating to a tracer substance being emitted with a substance to a defined area, sensing or measuring a tracer substance being emitted to a defined area associated with the emission management component 400, sensing or measuring environmental conditions associated with the defined area, determining an amount of a tracer substance being emitted to the defined area, determining an amount of a substance to be emitted to the defined area, a defined ratio of a tracer substance to a substance, determining whether and/or how much of an adjustment is to be made to the amount of a substance being emitted to the defined area, mappings, policies, defined substance criteria, algorithms (e.g., a defined substance emission control algorithm), protocols, interfaces, tools, and/or other information, to facilitate operation of the emission management component 400, as more fully disclosed herein, and control data flow between the emission management component 400 and other components (e.g., emitter component, storage component, communication network, an application, a server or other communication device, a cloud, . . . ) associated with the emission management component 400.

The data store 418 can store data structures (e.g., user data, metadata), code structure(s) (e.g., modules, objects, hashes, classes, procedures) or instructions, information relating to a tracer substance being emitted with a substance to a defined area, sensing or measuring a tracer substance being emitted to a defined area associated with the emission management component 400, sensing or measuring environmental conditions associated with the defined area, determining an amount of a tracer substance being emitted to the defined area, determining an amount of a substance to be emitted to the defined area, a defined ratio of a tracer substance to a substance, determining whether and/or how much of an adjustment is to be made to the amount of a substance being emitted to the defined area, mappings, policies, defined substance criteria, algorithms, protocols, interfaces, tools, and/or other information, to facilitate controlling operations associated with the emission management component 400. In an aspect, the processor component 416 can be functionally coupled (e.g., through a memory bus) to the data store 418 in order to store and retrieve information desired to operate and/or confer functionality, at least in part, to the communicator component 402, aggregator component 404, analyzer component 406, controller component 408, measurement component 410, emission determination component 412, adjuster component 414, etc., and/or substantially any other operational aspects of the emission management component 400.

In accordance with various embodiments of the disclosed subject matter, components (e.g., emitter component, substance sensor component, environment sensor component, emission management component, . . . ) of a system (e.g., substance emission system) can be situated or implemented on a single IC die or chip. An IC chip can be a CMOS chip, for example. In accordance with various other embodiments, the components of the system can be implemented on an ASIC chip. In accordance with still other embodiments, the components of the system can be situated or implemented on multiple IC dies or chips.

The aforementioned devices and/or systems have been described with respect to interaction between several components. It should be appreciated that such systems and components can include those components or sub-components specified therein, some of the specified components or sub-components, and/or additional components. Sub-components could also be implemented as components coupled to and/or communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

FIGS. 5-8 illustrate methods and/or flow diagrams in accordance with the disclosed subject matter. For simplicity of explanation, the methods are depicted and described as a series of acts. It is to be understood and appreciated that the subject disclosure is not limited by the acts illustrated and/or by the order of acts, for example acts can occur in various orders and/or concurrently, and with other acts not presented and described herein. Furthermore, not all illustrated acts may be required to implement the methods in accordance with the disclosed subject matter.

Figure 5:
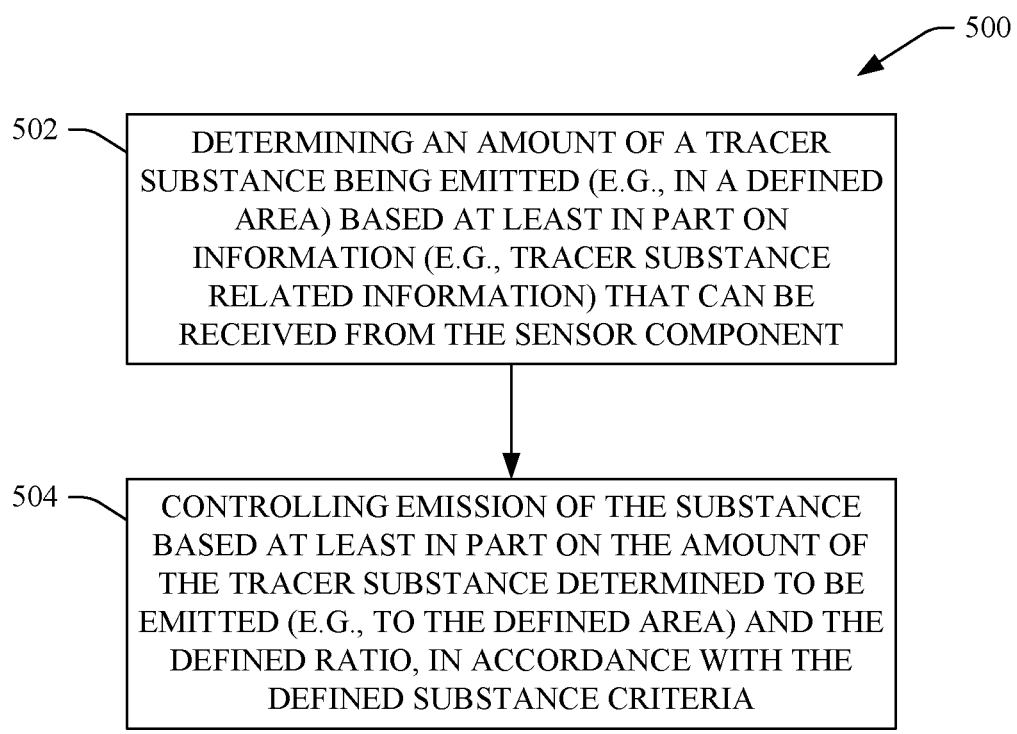
FIG. 5 illustrates a flow diagram of an example method for controlling an amount of a substance being emitted, in accordance with various aspects and embodiments of the disclosed subject matter.

Referring to FIG. 5, illustrated is a flow diagram of an example method 500 for controlling an amount of a substance (e.g., a scented or aromatic substance) being emitted, in accordance with various aspects and embodiments of the disclosed subject matter. The method 500 can be implemented by a system or device comprising an emission management component and a sensor component, for example.

At 502, an amount of a tracer substance being emitted (e.g., in a defined area) can be determined based at least in part on information (e.g., tracer substance related information) that can be received from the sensor component. The emission management component can receive the information from the sensor component. The emission management component can analyze the information, and can determine the amount of the tracer substance being emitted (e.g., by the system or device to the defined area) based at least in part on the results of the analyzing the information.

At 504, emission of the substance can be controlled based at least in part on the amount of the tracer substance determined to be emitted (e.g., to the defined area) and the defined ratio, in accordance with the defined substance criteria. The emission management component can control the amount of emission of the substance based at least in part on the amount of the tracer substance determined to be emitted and the defined ratio. For instance, in response to determining that the amount of the substance being emitted (e.g., to the defined area) is too high based at least in part on the amount of the tracer substance determined to be emitted and the defined ratio, the emission management component can control the emission of the substance to adjust (e.g., reduce) the amount of the substance being emitted, in accordance with the defined substance criteria. Alternatively, in response to determining that the amount of the substance being emitted (e.g., to the defined area) is too low (or is at an appropriate level) based at least in part on the amount of the tracer substance determined to be emitted and the defined ratio, the emission management component can control the emission of the substance to increase (or maintain at the same level) the amount of the substance being emitted, in accordance with the defined substance criteria.

Figure 6:
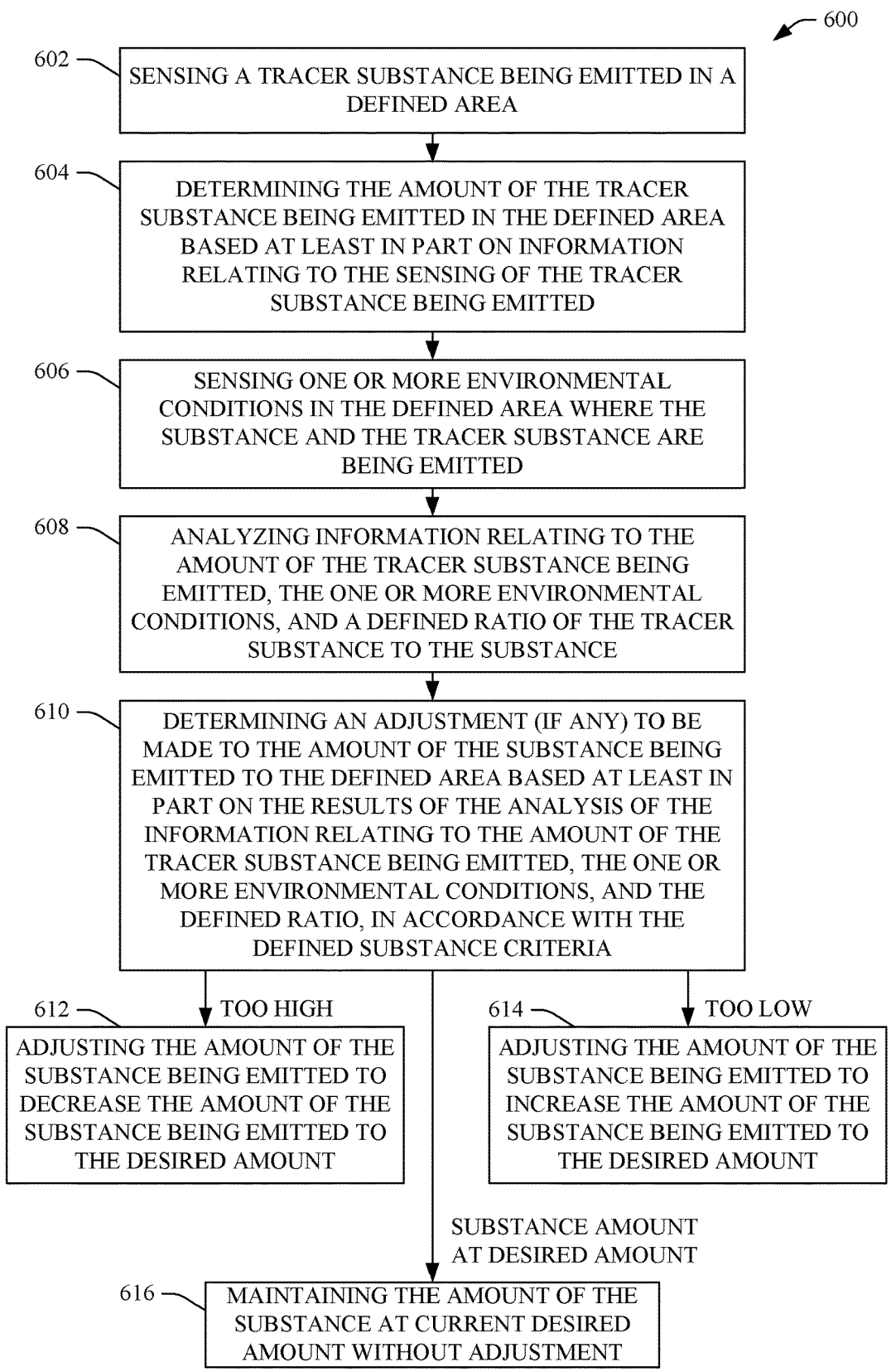
FIG. 6 depicts a flow diagram of another example method for controlling an amount of a substance (e.g., a scented or aromatic substance) being emitted, in accordance with various aspects and embodiments of the disclosed subject matter.

Turning to FIG. 6, depicted is a flow diagram of another example method 600 for controlling an amount of a substance (e.g., a scented or aromatic substance) being emitted, in accordance with various aspects and embodiments of the disclosed subject matter. The method 600 can be implemented by a system or device comprising an emission management component and a sensor component, which can comprise a substance sensor component and an environment sensor component, for example.

At 602, a tracer substance being emitted in a defined area can be sensed. A sensor component, which can comprise a substance sensor component, can sense, detect, and/or measure (e.g., measure the amount of) the tracer substance being emitted by an emitter component in the defined area. The sensor component can generate information (e.g., tracer substance related information) that can indicate the amount of the tracer substance being emitted based at least in part on the sensing of the tracer substance.

At 604, the amount of the tracer substance being emitted in the defined area can be determined based at least in part on information relating to the sensing of the tracer substance being emitted. The emission management component can determine the amount of the tracer substance being emitted in the defined area based at least in part on the information (e.g., tracer substance related information) relating to the sensing of the tracer substance being emitted.

At 606, one or more environmental conditions in the defined area where the substance and the tracer substance are being emitted can be sensed. The environment sensor component can sense the one or more environmental conditions (e.g., temperature, humidity level, air pressure level, air flow level or wind speed) in the defined area where the substance and the tracer substance are being emitted.

At 608, information relating to the amount of the tracer substance being emitted, the one or more environmental conditions, and a defined ratio of the tracer substance to the substance can be analyzed. The emission management component can analyze the information relating to the amount of the tracer substance being emitted, the one or more environmental conditions, and the defined ratio of the tracer substance to the substance to facilitate determining whether to adjust the amount of the substance being emitted to the defined area. The emission management component can know beforehand the defined ratio of a first portion of the tracer substance to a second portion of the substance being emitted by the emitter component to the defined area.

At 610, an adjustment (if any) to the amount of the substance being emitted to the defined area can be determined based at least in part on the results of the analysis of the information relating to the amount of the tracer substance being emitted, the one or more environmental conditions, and the defined ratio, in accordance with the defined substance criteria. The emission management component can determine the amount of the substance being emitted based at least in part on the results of the analysis of the information relating to the amount of the tracer substance being emitted and the defined ratio. The emission management component also can determine a desired (e.g., appropriate, suitable, acceptable, optimal) amount of the substance that should be emitted to the defined area based at least in part on the results of the analysis of the information relating to the one or more environmental conditions, in accordance with the defined substance criteria. The emission management component can compare the amount of the substance being emitted to the defined area with the desired amount of the substance that should be emitted to the defined area.

At 612, in response to determining that the amount of the substance being emitted to the defined area is too high, the amount of the substance being emitted can be adjusted to decrease the amount of the substance being emitted to the desired amount. Alternatively, at 614, in response to determining that the amount of the substance being emitted to the defined area is too low, the amount of the substance being emitted can be adjusted to increase the amount of the substance being emitted to the desired amount. Alternatively, at 616, in response to determining that the amount of the substance being emitted to the defined area is at the desired amount, the amount of the substance being emitted can be maintained at its current desired amount.

Based on the results of the comparing of the amount of the substance being emitted to the defined area with the desired amount of the substance that should be emitted to the defined area, and the defined substance criteria, the emission management component can determine whether there is a difference between the amount of the substance being emitted and the desired amount of the substance. If the emission management component determines that the amount of the substance being emitted to the defined area is too high, the emission component can adjust (e.g., reduce, decrease) the amount of the substance being emitted to the desired amount. If the emission management component determines that the amount of the substance being emitted to the defined area is too low, the emission management component can adjust (e.g., increase) the amount of the substance being emitted to the desired amount. If the emission management component determines that the amount of the substance being emitted to the defined area is at the desired amount, the emission management component can determine that no adjustment is to be made to the amount of the substance being emitted. The emission management component can generate instructions and send the instructions to the emitter component to facilitate controlling operation of the emitter component, or can otherwise control operation of the emitter component, to have the emitter component emit the substance (and the tracer substance) to the defined area at the desired amount of the substance.

Figure 7:
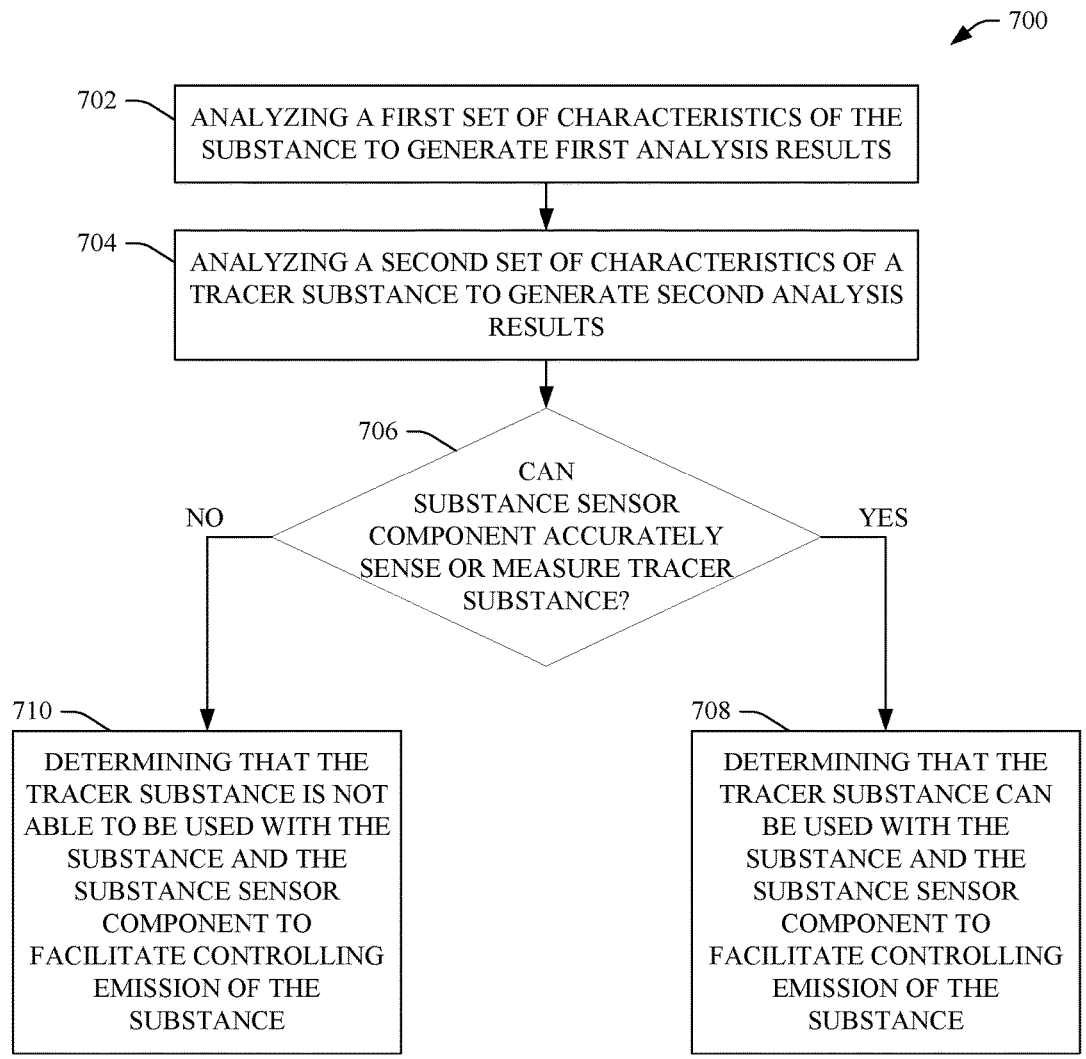
FIG. 7 illustrates a flow diagram of an example method for determining a tracer substance that can be added to a substance to be emitted to facilitate controlling emission of the substance, in accordance with various aspects and embodiments of the disclosed subject matter.

Referring to FIG. 7, illustrated is a flow diagram of an example method 700 for determining a tracer substance that can be added to a substance (e.g., a scented or aromatic substance) to be emitted to facilitate controlling emission of the substance, in accordance with various aspects and embodiments of the disclosed subject matter. The method 700 can be implemented by a system or device that can comprise, for example, an emission management component or another component(s).

At 702, a first set of characteristics of the substance can be analyzed to generate first analysis results. The emission management component or the other component(s) (e.g., substance analysis component) can identify and analyze the first set of characteristics of the substance, and can generate the first analysis results relating to the first set of characteristics of the substance based at least in part on the analysis. The substance can comprise a single substance or a combination of substances (e.g., the combination of two or more substances comprising at least the substance and a second substance).

At 704, a second set of characteristics of a tracer substance can be analyzed to generate second analysis results. The emission management component or the other component(s) can identify and analyze the second set of characteristics of the tracer substance under consideration, and can generate the second analysis results relating to the second set of characteristics of the tracer substance based at least in part on the analysis of the tracer substance. As part of this analysis, the emission management component or the other component(s) can analyze or evaluate the ability of a sensor substance component to accurately sense and/or measure an amount of the tracer substance being emitted with the substance when the tracer substance is mixed with the substance.

At 706, a determination can be made regarding whether a substance sensor component can accurately sense and/or measure an amount of the tracer substance being emitted with the substance when the tracer substance is mixed with the substance, based at least in part on the first analysis results and the second analysis results, in accordance with the defined substance criteria. For instance, the emission management component or the other component(s) can determine whether the substance sensor component can accurately sense and/or measure the amount of the tracer substance being emitted with the substance when the tracer substance is mixed with the substance, in accordance with the defined substance criteria.

If, at 706, it is determined that the substance sensor component can accurately sense and/or measure the amount of the tracer substance being emitted with the substance when the tracer substance is mixed with the substance, at 708, it can be determined that the tracer substance can be used with the substance and the substance sensor component to facilitate controlling emission of the substance. In response to determining that the substance sensor component can accurately sense and/or measure the amount of the tracer substance being emitted with the substance when the tracer substance is mixed with the substance, the emission management component or the other component(s) can determine that the tracer substance can be used with the substance and the substance sensor component to facilitate controlling emission of the substance.

Alternatively, if, at 706, it is determined that the substance sensor component is not able to accurately sense and/or measure the amount of the tracer substance being emitted with the substance when the tracer substance is mixed with the substance, at 710, it can be determined that the tracer substance is not able to be used with the substance and the substance sensor component to facilitate controlling emission of the substance. In response to determining that the substance sensor component is not able to accurately sense and/or measure the amount of the tracer substance being emitted with the substance when the tracer substance is mixed with the substance, the emission management component or the other component(s) can determine that the tracer substance is not able to be used with the substance and the substance sensor component to facilitate controlling emission of the substance.

The method 700 can be employed to evaluate various types of potential tracer substances and/or various types of substance sensor components with regard to the substance (or the combination of substances) to facilitate identifying a desirable tracer substance and/or a desirable substance sensor component that can be used to facilitate controlling emission of the substance (or the combination of substances), for example, in a defined area.

Figure 8:
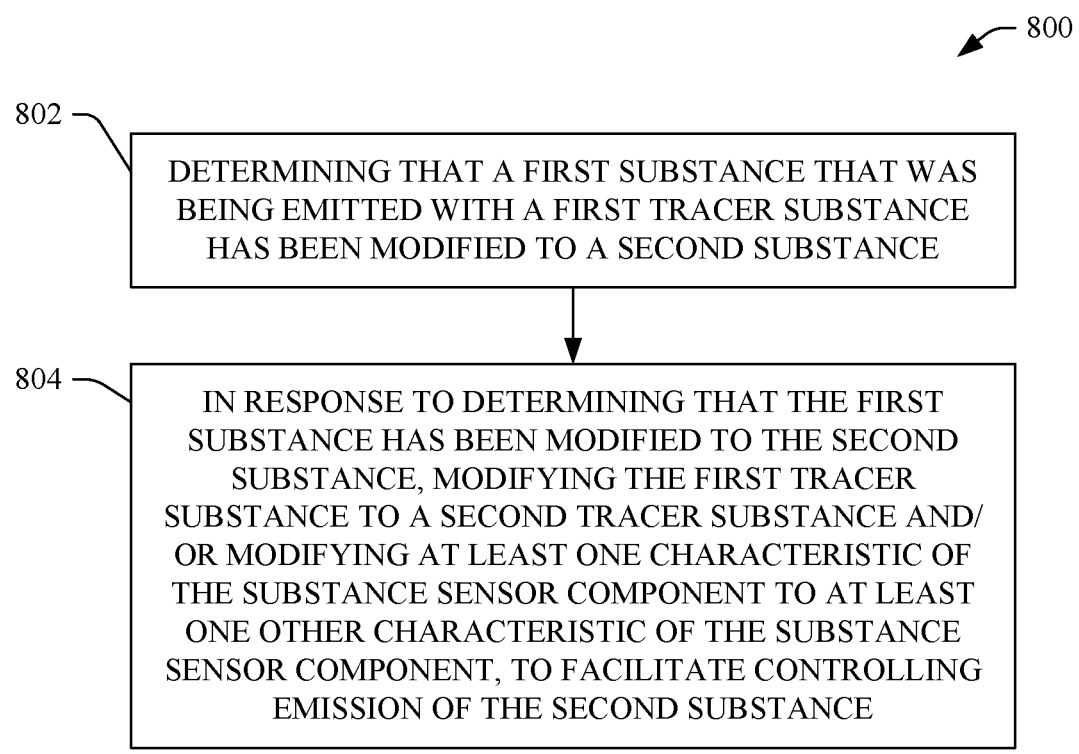
FIG. 8 depicts a flow diagram of an example method for modifying a substance sensor component or a tracer substance to facilitate controlling emission of a substance, in accordance with various aspects and embodiments of the disclosed subject matter.

FIG. 8 depicts a flow diagram of an example method 800 for modifying a substance sensor component or a tracer substance to facilitate controlling emission of a substance, in accordance with various aspects and embodiments of the disclosed subject matter. The method 800 can be implemented by a system or device comprising an emission management component and/or a substance sensor component, for example.

At 802, it can be determined that a first substance that was being emitted with a first tracer substance has been modified to a second substance. The emission management component or another component can modify the first substance to the second substance. For instance, the first substance can be changed to, modified to, or replaced with a second substance, or one or more other substances can be combined with the first substance to form the second substance, wherein the second substance can replace the first substance such that the second substance can be emitted (e.g., to a defined area) by an emitter component, instead of the first substance. The first tracer substance can be a tracer substance that was mixed with the first substance and can be used to facilitate controlling the emission of the first substance, for example, in a defined area, in accordance with the defined substance criteria, as more fully disclosed herein. The emission management component can detect or determine that the first substance that was being emitted to the first tracer substance has been modified to the second substance.

At 804, in response to determining that the first substance has been modified to the second substance, the first tracer substance can be modified to a second tracer substance and/or at least one characteristic of the substance sensor component can be modified to at least one other characteristic of the substance sensor component, to facilitate controlling emission of the second substance. In response to determining that the first substance has been modified to the second substance, the emission management component or another component can modify the first tracer substance to the second tracer substance and/or can modify at least one characteristic of the substance sensor component (e.g., a characteristic(s) or parameter setting(s) relating to temperature, humidity, or another characteristic) to at least one other characteristic of the substance sensor component, to facilitate controlling emission of the second substance.

For instance, the emission management component or another component can analyze the respective characteristics of the first substance, the second substance, the first tracer substance, the second tracer substance, and/or the substance sensor component to generate analysis results. The emission management component or another component can determine whether to modify the first tracer substance to the second tracer substance, determine the second tracer substance to use in connection with the second substance, determine whether to modify the at least one characteristic of the substance sensor component to the at least one other characteristic of the substance sensor component, and/or determine the at least one other characteristic of the substance sensor component to be used in connection with the second tracer substance and the second substance, based at least in part on the analysis results, in accordance with the defined substance criteria.

It is to be appreciated and understood that components (e.g., emission management component, sensor component, substance sensor component, emitter component, storage component, library component, processor component, data store, etc.), as described with regard to a particular device, system, or method, can include the same or similar functionality as respective components (e.g., respectively named components or similarly named components) as described with regard to other devices, systems, or methods disclosed herein.

Although the description has been provided with respect to particular embodiments thereof, these particular embodiments are merely illustrative and not restrictive.

While particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As used in this application, the terms "component," "system," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

What has been described above includes examples of aspects of the disclosed subject matter. It is, of course, not possible to describe every conceivable combination of components or methods for purposes of describing the disclosed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has," or "having," or variations thereof, are used in either the detailed description or the claims, such terms are intended to be inclusive in a manner similar to the term "comprising" as "comprising" is interpreted when employed as a transitional word in a claim.

What is claimed is:

1. A system, comprising:
   a substance sensor component that senses an amount of a first tracer substance being emitted with a substance; and
   an emission management component that controls emission of the substance based at least in part on the amount of the first tracer substance being emitted, wherein, in response to determining that a second tracer substance has been changed to the first tracer substance, the emission management component modifies a characteristic of the substance sensor component to enable the substance sensor component to sense the first tracer substance.

2. The system of claim 1, wherein the first tracer substance is added to the substance to form a first mixture having a defined ratio of a first concentration of the first tracer substance to a second concentration of the substance, and wherein the emission management component determines a disparate amount of the substance being emitted with the amount of the first tracer substance based at least in part on the amount of the first tracer substance and the defined ratio.

3. The system of claim 2, wherein the first tracer substance is added to the substance and a second substance to form a first mixture having the defined ratio of the first concentration of the first tracer substance to the second concentration of the substance and a second defined ratio of the first concentration of the first tracer substance to a third concentration of the second substance, wherein the emission management component controls emission of the substance and the second substance based at least in part on the amount of the first tracer substance being emitted, the defined ratio, and the defined second ratio, and wherein the emission management component determines respective amounts of the substance and the second substance being emitted with the amount of the first tracer substance based at least in part on the amount of the first tracer substance determined to have been emitted, the defined ratio, and the defined second ratio.

4. The system of claim 3, wherein the emission management component adjusts at least one characteristic of the substance sensor component, based at least in part on at least one attribute of the second substance, to facilitate accurate sensing of the first tracer substance, by the sensor component, in the first mixture of the first tracer substance, the substance, and the second substance.

5. The system of claim 2, wherein the emission management component controls emission of a second substance based at least in part on a second amount of a second tracer substance being emitted and a defined second ratio, wherein the second tracer substance is added to the second substance to form a second mixture having the defined second ratio of a third concentration of the second tracer substance to a fourth concentration of the second substance, and wherein the emission management component determines a particular amount of the second substance being emitted with the second amount of the second tracer substance based at least in part on the second amount of the second tracer substance and the defined second ratio.

6. The system of claim 1, further comprising:
a substance storage component that stores the substance and the first tracer substance, wherein the first tracer substance is mixed with the substance to form a first mixture having a defined ratio of a first concentration of the first tracer substance to a second concentration of the substance; and
an emitter component that emits the substance and the first tracer substance based at least in part on the defined ratio of the first concentration of the first tracer substance to the second concentration of the substance.

7. The system of claim 1, wherein the substance comprises an aromatic scent.

8. The system of claim 1, wherein the first tracer substance is determined to be at least one of odorless with respect to an olfactory sense of a person, safe with respect to the person, or colorless with respect to the person, in accordance with defined substance criteria relating to at least one of odor, safety, or color.

9. The system of claim 1, further comprising an environment sensor component that senses environmental conditions in a defined area in proximity to the environment sensor component.

10. The system of claim 9, wherein the emission management component controls the emission of the substance based at least in part on the amount of the first tracer substance being emitted and the environmental conditions sensed in the defined area.

11. The system of claim 9, wherein the environment sensor component senses at least one of a temperature, a humidity level, an air pressure level, or an air flow level, in the defined area in proximity to the environment sensor component.

12. The system of claim 11, wherein the emission management component controls the emission of the substance based at least in part on the amount of the first tracer substance being emitted and at least one of the temperature, the humidity level, the air pressure level, or the air flow level, in the defined area.

13. The system of claim 9, wherein the environment sensor component comprises at least one of a temperature sensor, a humidity sensor, an air pressure sensor, or an air flow sensor.

14. The system of claim 1, further comprising:
a library component that comprises information relating to at least one of substances, tracer substances, substance sensor components, defined ratios relating to the substances and the tracer substances, or mappings associated with the tracer substances, wherein the tracer substances comprise the first tracer substance, the substance sensor components comprise the substance sensor component, and the substances comprise the substance.

15. The system of claim 14, wherein the emission management component at least one of receives or generates the information, comprising a subset of the information relating to the first tracer substance and the substance, and controls the emission of the substance based at least in part on the subset of the information and the amount of the first tracer substance being emitted.

16. The system of claim 14, wherein the information comprises a subset of the information, and wherein the subset of the information comprises a mapping of the first tracer substance to at least one of the substance sensor component, an adjustment of the substance sensor component, the substance, or a defined ratio of a first portion of the first tracer substance to a second portion of the substance.

17. A system, comprising:
means for sensing a level of a first tracer substance being emitted with a substance; and
means for controlling emission of the substance based at least in part on the level of the first tracer substance being emitted, wherein, in response to determining that a second tracer substance has been changed to the first tracer substance, the means for controlling changes a characteristic of the means for sensing to enable the means for sensing to sense the first tracer substance.

18. The system of claim 17, wherein the first tracer substance is mixed with the substance to form a mixture having a defined ratio of a first amount of the first tracer substance to a second amount of the substance, and wherein the means for controlling comprises means for determining a respective level of the substance being emitted with the level of the first tracer substance based at least in part on the level of the first tracer substance and the defined ratio.

19. A method, comprising:
   sensing, by a sensor of a system comprising a processor, an amount of a first tracer substance being emitted with a substance, wherein, in response to a second tracer substance being changed to the first tracer substance, a characteristic of the sensor is modified to enable the sensor to sense the first tracer substance; and
   managing, by the system, the emitting of the substance based at least in part on the amount of the first tracer substance being emitted.

20. The method of claim 19, wherein the first tracer substance is added to the substance to form a mixture having a defined ratio of a first concentration of the first tracer substance to a second concentration of the substance, and wherein the method further comprises:
   determining, by the system, a disparate amount of the substance being emitted with the amount of the first tracer substance based at least in part on the amount of the first tracer substance and the defined ratio.

* * * * *